United States Patent
Yoshino

(10) Patent No.: US 8,786,690 B2
(45) Date of Patent: Jul. 22, 2014

(54) IMAGING APPARATUS, ENDOSCOPE SYSTEM, AND METHOD OF CONTROLLING IMAGING APPARATUS

(75) Inventor: Koichiro Yoshino, Tokyo (JP)

(73) Assignee: Olympus Corporation, Tokyo (JP)

(*) Notice: Subject to any disclaimer, the term of this patent is extended or adjusted under 35 U.S.C. 154(b) by 567 days.

(21) Appl. No.: 13/013,112

(22) Filed: Jan. 25, 2011

(65) Prior Publication Data

US 2011/0184236 A1    Jul. 28, 2011

(30) Foreign Application Priority Data

Jan. 25, 2010   (JP) .................................. 2010-013034

(51) Int. Cl.
| | |
|---|---|
| A61B 1/04 | (2006.01) |
| G03B 13/00 | (2006.01) |
| H04N 5/232 | (2006.01) |
| A61B 1/05 | (2006.01) |
| A61B 1/045 | (2006.01) |
| A61B 1/00 | (2006.01) |
| A61B 1/07 | (2006.01) |
| A61B 1/06 | (2006.01) |

(52) U.S. Cl.
CPC ... *A61B 1/05* (2013.01); *A61B 1/07* (2013.01); *A61B 1/045* (2013.01); *A61B 1/00188* (2013.01); *A61B 1/0646* (2013.01)
USPC .............. 348/74; 348/345; 348/45; 348/65; 600/109; 396/102

(58) Field of Classification Search
CPC ...................................... A61B 1/05; A61B 1/07
USPC ..................................... 348/74, 345; 396/102
See application file for complete search history.

(56) References Cited

U.S. PATENT DOCUMENTS

| | | | | |
|---|---|---|---|---|
| 2002/0055669 | A1* | 5/2002 | Konno | 600/167 |
| 2010/0165176 | A1* | 7/2010 | Taniguchi | 348/345 |

FOREIGN PATENT DOCUMENTS

| | | | | |
|---|---|---|---|---|
| JP | 02-274073 | * | 11/1990 | H04N 5/238 |
| JP | 2007-13269 A | | 1/2007 | |
| JP | 2007-013270 | * | 1/2007 | H04N 5/232 |

OTHER PUBLICATIONS

Chinese Office Action dated Mar. 13, 2014 from related Chinese Application No. 201110025797.7, together with an English language translation.

* cited by examiner

*Primary Examiner* — Andy Rao
*Assistant Examiner* — Nguyen Truong
(74) *Attorney, Agent, or Firm* — Scully, Scott, Murphy & Presser, P.C.

(57) ABSTRACT

An imaging apparatus includes an imaging section that images an object, an observation mode setting section that sets an observation mode when the imaging section images the object, and a control section that controls an image read mode in which an image is read from the imaging section and a in-focus object plane of the imaging section based on the observation mode set by the observation mode setting section.

14 Claims, 14 Drawing Sheets

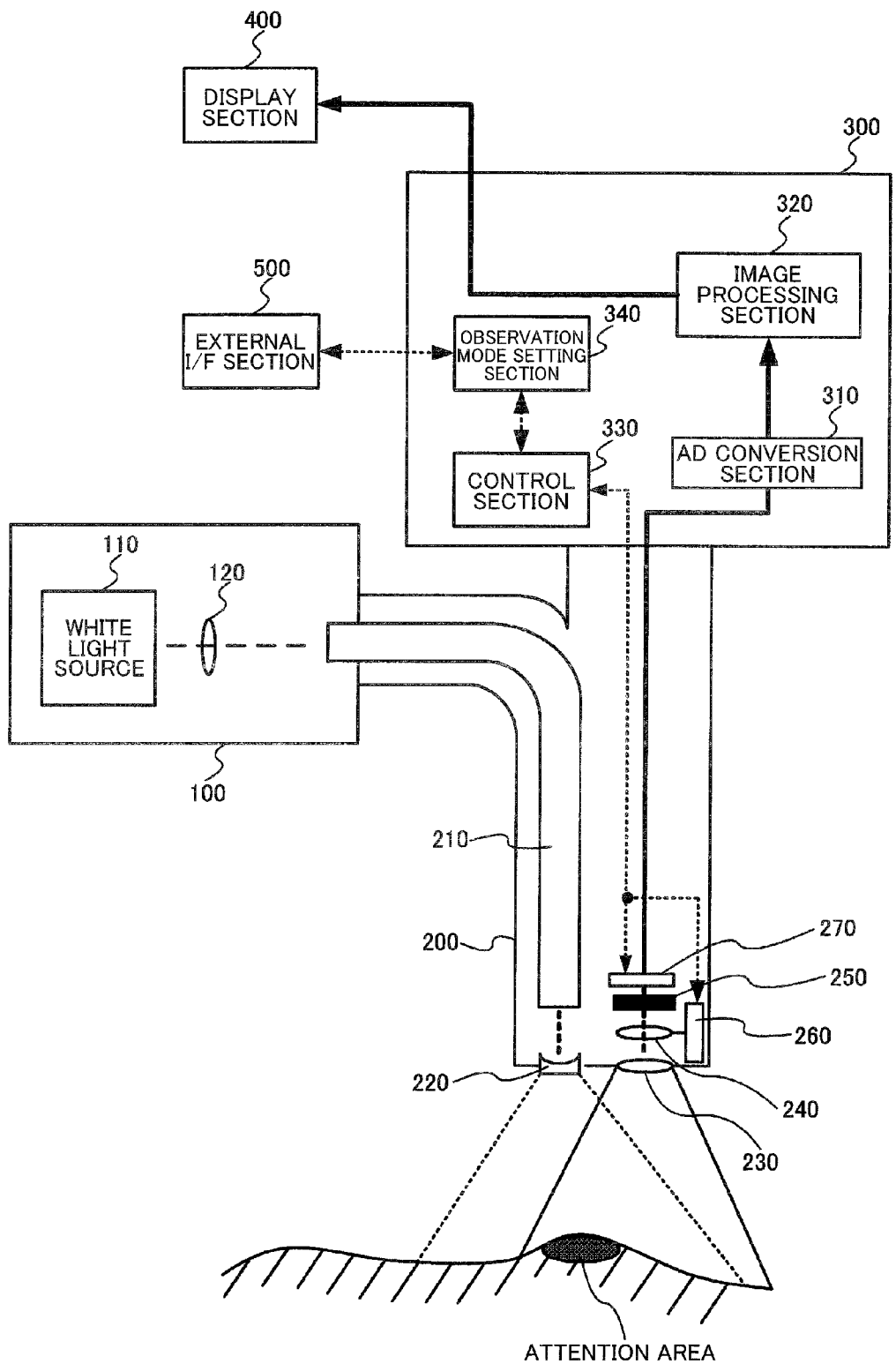

FIG. 8A  DISTANT OBSERVATION MODE
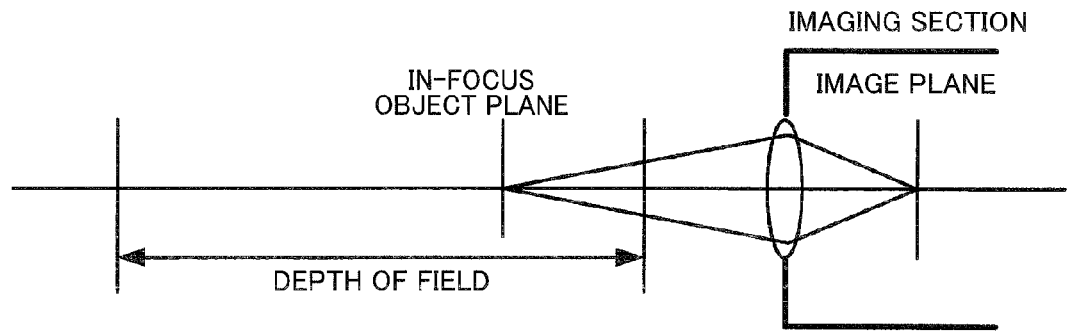
FIG. 8B  ALL-PIXEL READ MODE+NO FOCUS ADJUSTMENT
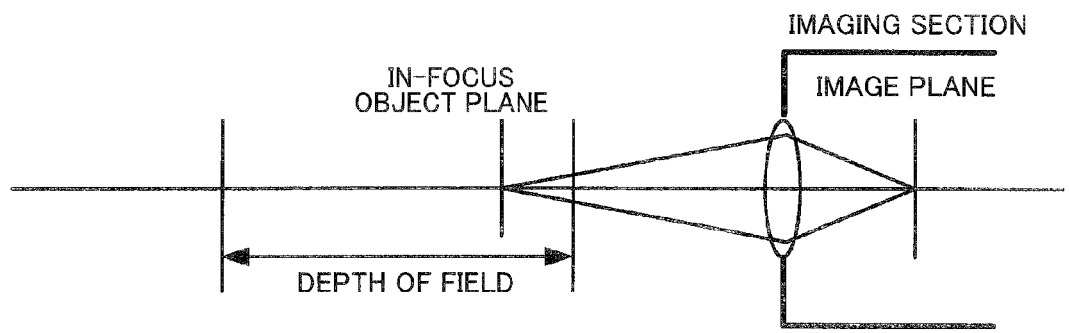
FIG. 8C  CLOSE OBSERVATION MODE
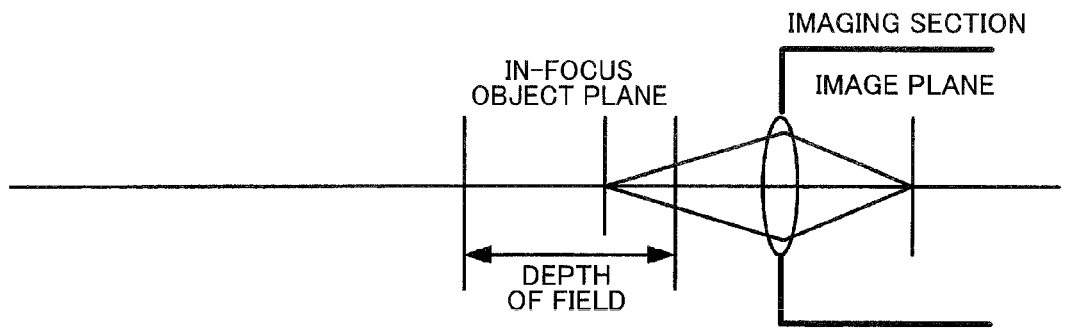

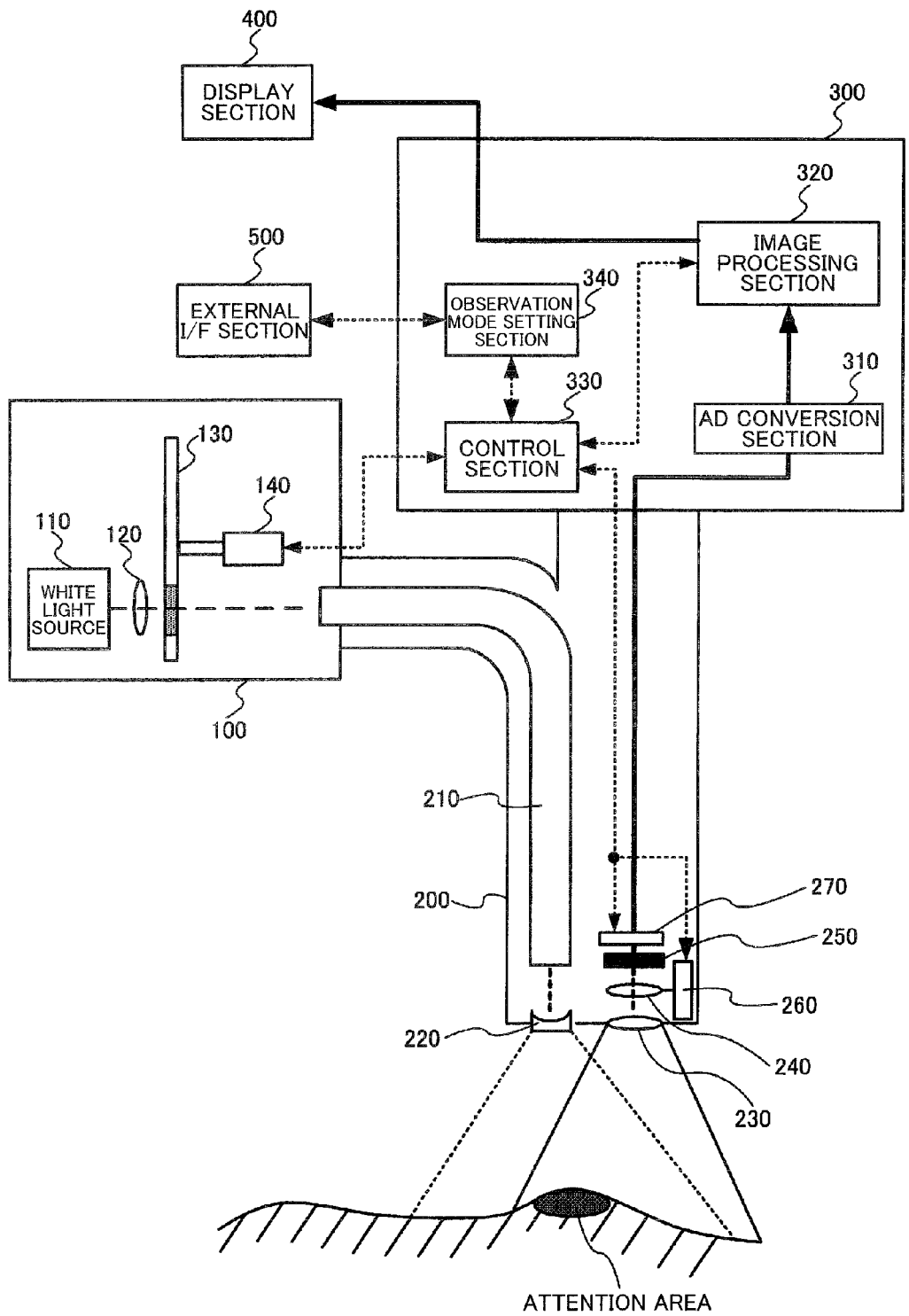

US 8,786,690 B2

IMAGING APPARATUS, ENDOSCOPE SYSTEM, AND METHOD OF CONTROLLING IMAGING APPARATUS

Japanese Patent Application No. 2010-013034 filed on Jan. 25, 2010, is hereby incorporated by reference in its entirety.

BACKGROUND

The present invention relates to an imaging apparatus, an endoscope system, a method of controlling an imaging apparatus, and the like.

An imaging apparatus such as an endoscope is desired to generate a deep-focus image in order to facilitate a doctor's diagnosis. In order to deal with such a demand, the depth of field of an endoscope is increased by utilizing an optical system having a relatively large F-number.

In recent years, an imaging element having about several hundred thousand pixels has been used for endoscope systems. The depth of field of an optical system is determined by the size of the permissible circle of confusion. Since an imaging element having a large number of pixels has a small pixel pitch and a small permissible circle of confusion, the depth of field of the imaging apparatus decreases. In this case, the depth of field may be maintained by reducing the aperture of the optical system, and increasing the F-number of the optical system. According to this method, however, the optical system darkens, noise increases, and the image quality deteriorates. Moreover, the effect of diffraction increases as the F-number increases, so that the imaging performance deteriorates. Accordingly, a high-resolution image cannot be obtained even if the number of pixels of the imaging element is increased. JP-A-2007-13270 discloses technology that changes a pixel binning read process between a movie and a still image.

SUMMARY

According to one aspect of the invention, there is provided an imaging apparatus comprising:
an imaging section that images an object;
an observation mode setting section that sets an observation mode when the imaging section images the object; and
a control section that controls an image read mode in which an image is read from the imaging section and a in-focus object plane of the imaging section based on the observation mode set by the observation mode setting section.

According to another aspect of the invention, there is provided an imaging apparatus comprising:
an imaging section that images an object;
an observation mode setting section that sets an observation mode when the imaging section images the object; and
a control section,
the control section variably controlling a depth of field even if a in-focus object plane of the imaging section is fixed when the observation mode has been set to a first observation mode.

According to another aspect of the invention, there is provided an endoscope system comprising:
an imaging section that images an object;
an observation mode setting section that sets an observation mode when the imaging section images the object; and
a control section that controls an image read mode in which an image is read from the imaging section and a in-focus object plane of the imaging section based on the observation mode set by the observation mode setting section.

According to another aspect of the invention, there is provided an endoscope system comprising:
an imaging section that images an object;
an observation mode setting section that sets an observation mode when the imaging section images the object; and
a control section that controls a depth of field of the imaging section and a in-focus object plane of the imaging section based on the observation mode set by the observation mode setting section.

According to another aspect of the invention, there is provided a method of controlling an imaging apparatus, the method comprising:
setting an observation mode when an object is imaged;
controlling an image read mode in which an image is read from an imaging section based on the set observation mode;
controlling a in-focus object plane of the imaging section based on the set observation mode; and
controlling the imaging apparatus so that the imaging apparatus images the object based on the image read mode and the control of the in-focus object plane.

BRIEF DESCRIPTION OF THE DRAWINGS

FIG. 3 shows a system configuration example according to one embodiment of the invention.

FIG. 8A is a view illustrative of the depth of field in a distant observation mode, FIG. 8B is a view illustrative of the depth of field when an all-pixel read process is performed without changing the in-focus object plane, and FIG. 8C is a view illustrative of the depth of field in a close observation mode.

FIG. 9 shows another system configuration example according to one embodiment of the invention.

DESCRIPTION OF EXEMPLARY EMBODIMENTS

Several aspects of the invention may provide an imaging apparatus, an endoscope system, a method of controlling an imaging apparatus, and the like that set an observation mode, and control a read mode and a in-focus object plane based on the set observation mode.

Several aspects of the invention may provide an imaging apparatus, an endoscope system, a method of controlling an imaging apparatus, and the like that set a close observation mode or a distant observation mode, and implement a wide depth of field in the distant observation mode by performing a pixel binning read process.

According to one embodiment of the invention, there is provided an imaging apparatus comprising:

an imaging section that images an object;

an observation mode setting section that sets an observation mode when the imaging section images the object; and a control section that controls an image read mode in which an image is read from the imaging section and a in-focus object plane of the imaging section based on the observation mode set by the observation mode setting section.

According to the above embodiment, the image read mode from the imaging section and the in-focus object plane of the imaging section are controlled based on the set observation mode. Therefore, the read mode and the in-focus object plane can be appropriately controlled depending on the photographic conditions in each observation mode.

According to another embodiment of the invention, there is provided an imaging apparatus comprising:

an imaging section that images an object;

an observation mode setting section that sets an observation mode when the imaging section images the object; and a control section, the control section variably controlling a depth of field even if a in-focus object plane of the imaging section is fixed when the observation mode has been set to a first observation mode.

According to the above embodiment, when the set observation mode is the first observation mode, the depth of field can be variably controlled even if the in-focus object plane is fixed.

Exemplary embodiments of the invention are described below. Note that the following embodiments do not in any way limit the scope of the invention laid out in the claims. Note also that all elements of the following embodiments should not necessarily be taken as essential requirements for the invention.

1. Method

A method according to one embodiment of the invention is described below with reference to FIGS. 1, 2A, and 2B.

Figure 1:
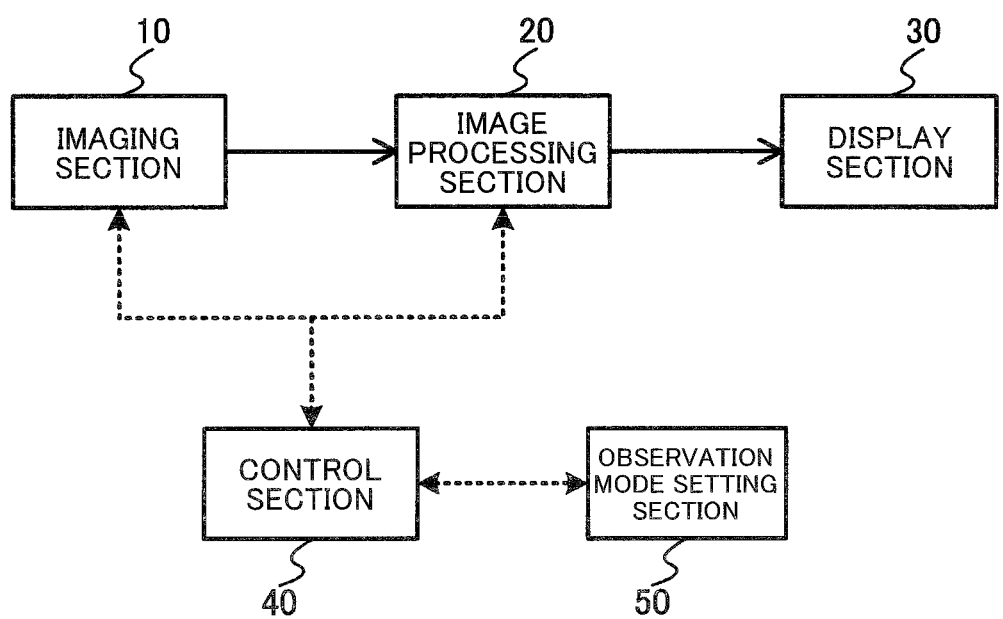
FIG. 1 shows a basic configuration example of an imaging apparatus according to one embodiment of the invention.

FIG. 1 is a block diagram showing a basic configuration example of an imaging apparatus according to this embodiment. The imaging apparatus includes an imaging section 10, an image processing section 20, a display section 30, a control section 40, and an observation mode setting section 50. Note that various modifications may be made, such as omitting some (e.g., display section) of the elements. The imaging apparatus according to this embodiment may be a digital camera, a digital video camera, or an endoscope system.

The imaging section 10 is connected to the image processing section 20, and the image processing section 20 is connected to the display section 30. The control section 40 is bidirectionally connected to the imaging section 10 and the image processing section 20. The control section 40 is also bidirectionally connected to the observation mode setting section 50.

The observation mode setting section 50 sets an observation mode, and transmits the set information to the control section 40. The control section 40 generates a control signal that causes the imaging section 10 and the image processing section 20 to perform an imaging process and an image process based on the observation mode set by the observation mode setting section 50.

Figure 2A:
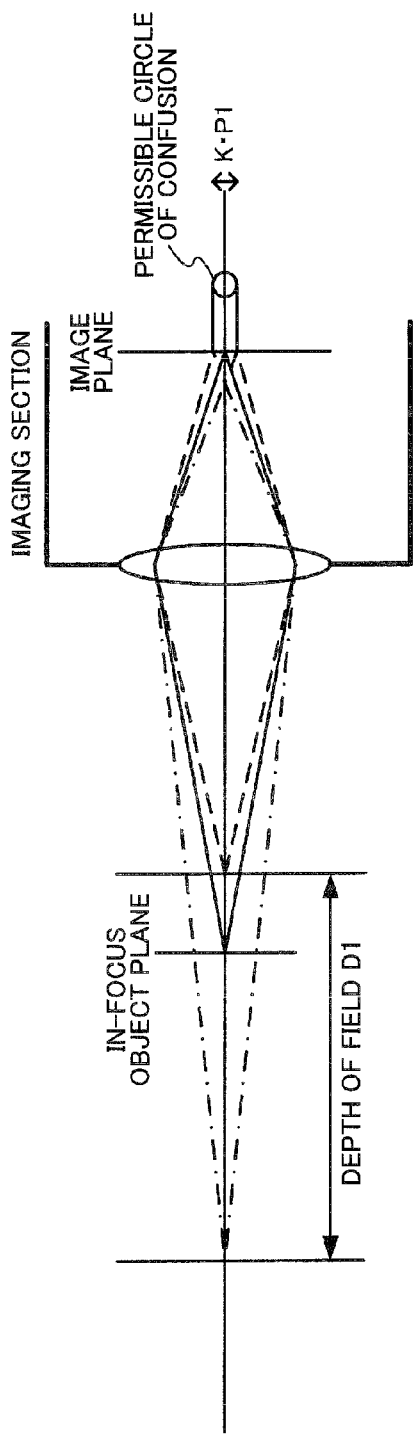
FIGS. 2A and 2B are views illustrative of an increase in depth of field due to an increase in pixel pitch.

When the pixel pitch corresponds to the actual pixel pitch of an imaging element of the imaging section 10, the in-focus object plane, the depth of field, and the permissible circle of confusion have the relationship shown in FIG. 2A. The mode shown in FIG. 2A fully utilizes the resolving power of the imaging element since the pixel pitch of the imaging element is directly used. The size of the permissible circle of confusion is expressed by K·P1 using a coefficient K determined by an element (e.g., filter). The depth of field D1 is determined by the permissible circle of confusion having the size K·P1.

However, the pixel pitch P1 decreases as the resolving power of the imaging apparatus increases, so that the depth of field D1 decreases. For example, the depth of field of an endoscope system must be increased in order to facilitate a doctor's diagnosis. However, the depth of field D1 shown in FIG. 2A that is deter mined by the actual pixel pitch of the imaging element cannot be increased.

In order to solve this problem, the applicant proposed setting a close observation mode and a distant observation mode, and utilizing the distant observation mode with a wide depth of field when deep focusing is necessary.

Figure 2B:
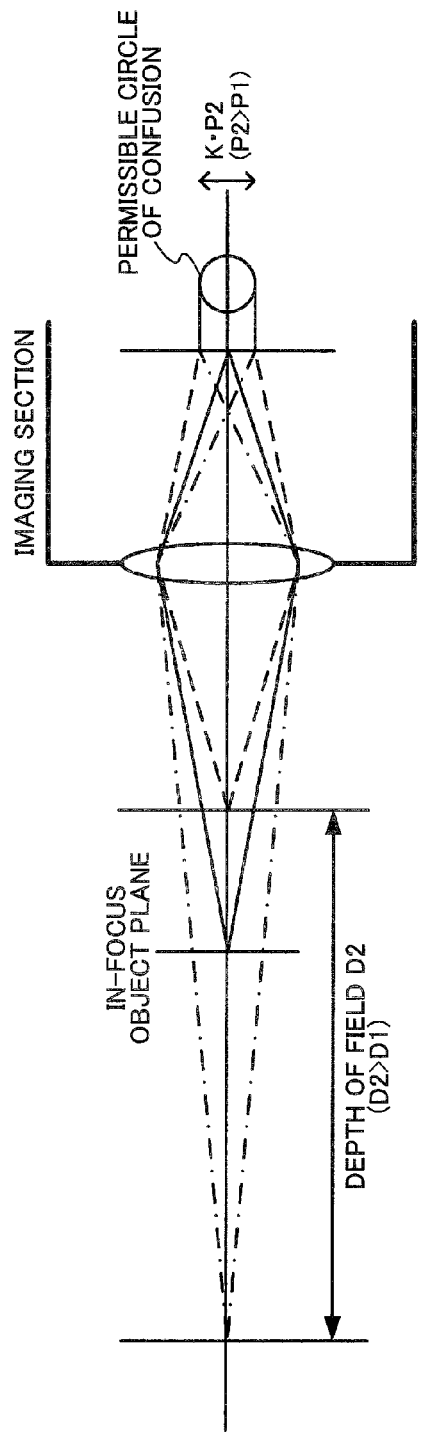
Figure 4A:
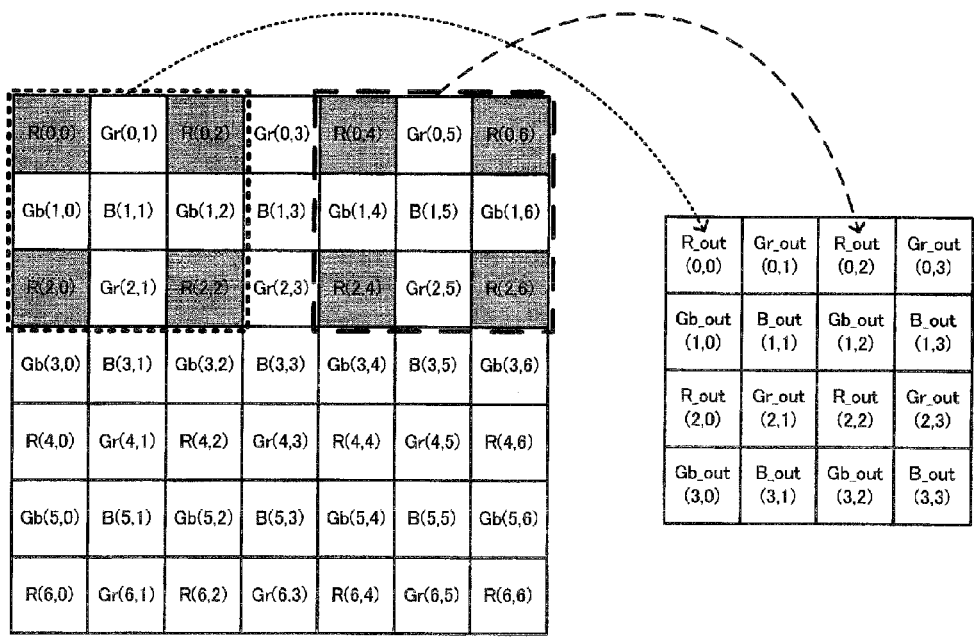
FIGS. 4A and 4B are views illustrative of an image when performing a pixel binning read process.
Figure 4B:
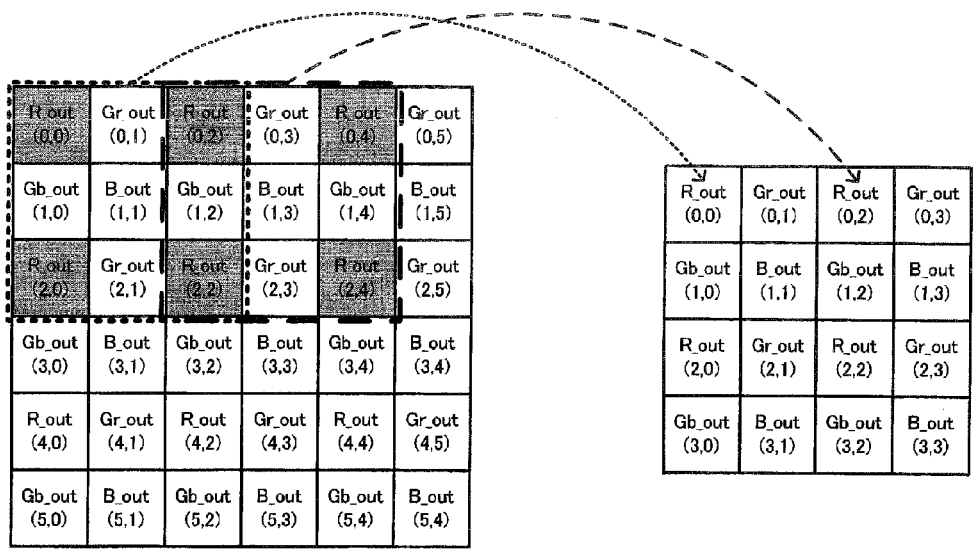

FIG. 2B shows an outline of the distant observation mode. The same optical system conditions are employed in FIGS. 2A and 2B. In the distant observation mode, a pixel pitch P2 shown in FIG. 2B corresponds to the pixel pitch when one pixel includes a plurality of pixels. This may be implemented by a pixel binning read process, for example. FIGS. 4A and 4B show the pixel binning read process. Specifically, the sum of the pixel values of four pixels R(0, 0), R(0, 2), R(2, 0), and R(2, 2) shown in FIG. 4A is calculated. The calculated value is referred to as R_out(0, 0). In FIG. 4A, a 3×3 pixel area including the above four pixels corresponds to the pixel R_out(0, 0) shown in FIG. 4B. Specifically, 3×3 pixels are handled as one pixel. When the pixel pitch in FIG. 4A is referred to as P, the pixel pitch is 3×P when using the pixel binning read process. In this case, the relationship "P2>P1" is satisfied, so that the size of the permissible circle of confusion can be increased. Therefore, the depth of field D2 is greater than the depth of field D1, as is clear from FIGS. 2A and 2B.

This makes it possible to use the close observation mode with a narrow depth of field and a high resolving power and the distant observation mode with a wide depth of field and a low resolving power. For example, an efficient diagnosis using an endoscope system can be implemented by appropriately switching the mode between the close observation mode and the distant observation mode depending on the situation.

Figure 16A:
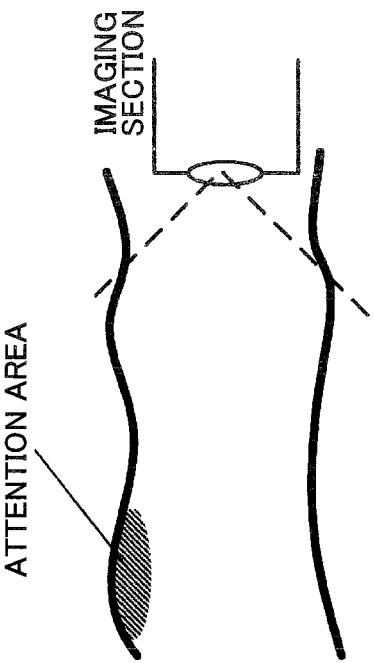
FIG. 16A is a view illustrative of a case where a hollow tubular object is imaged.

For example, the distant observation mode may be used when searching for a lesion area, and the close observation mode may be used for close observation of the lesion area that has been found. As shown in FIG. 16A, the imaging section moves through a hollow tubular object when searching for a lesion area, for example. The distance between the imaging section and the object varies to a large extent. In this case, if the depth of field is narrow, only part of the object is in focus (i.e., the remaining area is out of focus). This makes it difficult to make an accurate diagnosis. In the distant observation mode with a wide depth of field, the object comes into focus even if the distance between the imaging section and the object varies. Therefore, the distant observation mode is effective when searching for a lesion area.

Figure 16B:
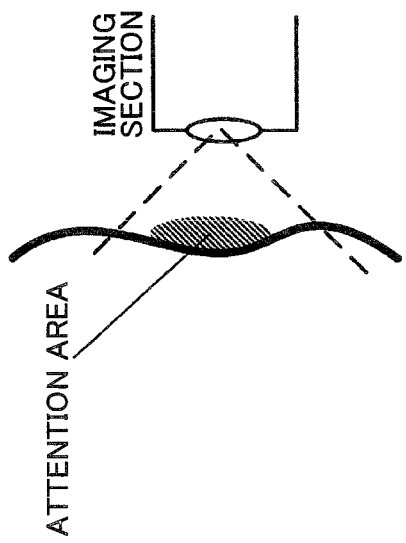
FIG. 16B is a view illustrative of a case where an imaging section faces an object.

When closely observing a lesion area that has been found, the lesion area may be observed through the imaging section that faces the lesion area (see FIG. 16B). Therefore, the doctor desires to observe the range that is positioned within a certain distance from the imaging section. Specifically, a problem rarely occurs even if the depth of field is narrow. On the other hand, a detailed image having a high resolution is required to make an accurate diagnosis. Therefore, an observed image that meets the doctor's demand can be provided by utilizing the close observation mode when closely observing the lesion area.

In recent years, the pixel pitch of imaging elements has decreased in order to deal with full high vision and the like. The user normally fully utilizes the performance of an imaging element produced by the most advanced production process. In this embodiment, the distant observation mode and the close observation mode are provided. In the distant observation mode, the depth of field is increased by handling a plurality of pixels as one pixel. This makes it possible to survey the object. In the close observation mode, the object can be observed with high resolution by fully utilizing the performance of the imaging element.

Note that a plurality of pixels may be handled as one pixel by a method other than the pixel binning read process. In the example shown in FIGS. 4A and 4B, the pixel value of a given pixel (e.g., R(0, 0)) may be used as the pixel value of the pixel R_out(0, 0) instead of calculating the sum (or the average value) of the pixel values of four pixels, for example. A similar effect may be achieved by a filter process performed by the image processing section 20 (the pixel binning read process is implemented by the imaging section 10). Specifically, a filter process may be performed so that the sum of the pixel values of a plurality of pixels is used as the pixel value of an output pixel.

First to fourth embodiments are described below. The following description is given taking an endoscope system as an example. Note that the imaging apparatus is not limited to an endoscope system, as described above.

2. First Embodiment

An endoscope system according to a first embodiment of the invention is described below with reference to FIG. 3. The endoscope system according to this embodiment includes a light source section 100, an imaging section 200, a processing section 300, a display section 400, and an external I/F section 500. Note that various modifications may be made, such as omitting some of the elements or adding other elements.

The light source section 100 includes a white light source 110 that emits (generates) white light, and a condenser lens 120 that focuses white light on a light guide fiber 210.

The imaging section 200 is formed to be elongated and flexible (i.e., can be curved) so that the imaging section 200 can be inserted into a body cavity or the like. The imaging section 200 includes the light guide fiber 210 that guides light focused by the light source section, an illumination lens 220 that diffuses light guided to the end of the imaging section 200 by the light guide fiber 210 so that the diffused light is applied to an observation target, an objective lens 230 that focuses light reflected from the observation target, a focus adjustment lens 240 that is used to adjust the in-focus object plane, an imaging element 250 that detects focused reflected light, a read mode control section 270 that controls a read mode when reading a signal from the imaging element, and outputs an analog signal, and a lens driver section 260 that drives the focus adjustment lens 240. Note that various modifications may be made, such as omitting some of the elements or adding other elements.

The lens driver section 260 is a stepping motor, for example. The lens driver section 260 is connected to the focus adjustment lens 240. The lens driver section 260 adjusts the in-focus object plane by changing the position of the focus adjustment lens. The imaging element 250 includes a Bayer array color filter shown in FIG. 4A. Note that Gr and Gb have identical spectral characteristics. The details of the read mode control section 270 are described later.

The processing section 300 includes an AD conversion section 310, an image processing section 320, a control section 330, and an observation mode setting section 340. Note that various modifications may be made, such as omitting some of the elements or adding other elements.

The AD conversion section 310 converts an analog signal output from the read mode control section 270 into a digital signal, and outputs the digital signal. The image processing section 320 performs an image process (e.g., white balance process, interpolation process (demosaicing process), color conversion process, and grayscale transformation process) on the digital signal output from the AD conversion section 310, and outputs an image to the display section 400. The observation mode setting section 340 determines the observation mode based on a control signal input from the external I/F section 500, and outputs observation mode information to the control section 330. The control section 330 controls the lens driver section 260 and the read mode control section 270 based on the received observation mode information.

The display section 400 is a liquid crystal monitor, for example. The display section 400 displays the image output from the image processing section 320.

The external I/F section 500 is an interface that allows the user to perform an input operation or the like on the imaging apparatus. The external I/F section 500 includes a power supply switch (power supply ON/OFF switch), a shutter button (photographing operation start button), a mode (e.g., photographing mode) change button, and the like. The external I/F section 500 outputs information about the observation mode to the observation mode setting section 340.

The details of the read mode control section 270 are described below. The read mode control section 270 receives an analog signal that is raster-scanned and output from the imaging element 250. The read mode control section 270 separates the input analog signal into four channels (R, Gr, Gb, and B) corresponding to the type of color filter. The read mode control section 270 performs a given process based on a read mode, synthesizes the signals in the same format as that of the analog signal that has been raster-scanned and output from the imaging element 250, and outputs the resulting signal.

The read mode control section 270 switches the read mode between an all-pixel read mode and a pixel binning read mode based on a control signal output from the control section 330. When the all-pixel read mode has been selected, the read mode control section 270 separates the input analog signal into four channels (R, Gr, Gb, and B) corresponding to the type of color filter, synthesizes the signals in the same format as that of the analog signal that has been output from the imaging element 250, and outputs the resulting signal.

When the pixel binning read mode has been selected, the read mode control section 270 separates the input analog signal into four channels (R, Gr, Gb, and B) corresponding to the type of color filter, and sums up the signal values of 2×2 pixels that are adjacent in the horizontal direction and the vertical direction corresponding to each channel. The signal values input to the read mode control section 270 from the imaging element 250 are summed up according to the following expressions (1). Note that $R(x, y)$, $Gr(x, y)$, $Gb(x, y)$, and $B(x, y)$ are input signal values, and $R\_out(x, y)$, $Gr\_out(x, y)$, $Gb\_out(x, y)$, and $B\_out(x, y)$ are signal values obtained by summing up the input signal values.

$$R\_out(x, y) = R(x, y) + R(x+2, y) + R(x, y+2) + R(x+2, y+2)$$

$$Gr\_out(x, y) = Gr(x, y) + Gr(x+2, y) + Gr(x, y+2) + Gr(x+2, y+2)$$

$$Gb\_out(x, y) = Gb(x, y) + Gb(x+2, y) + Gb(x, y+2) + Gb(x+2, y+2)$$

$$B\_out(x, y) = B(x, y) + B(x+2, y) + B(x, y+2) + B(x+2, y+2) \quad (1)$$

The expressions (1) are described below with reference to FIG. 4A. For example, when calculating the signal value R_out(0, 0), four R signal values R(0, 0), R(2, 0), R(0, 2), and R(2, 2) included in a 3×3 area are summed up. When calculating the signal value R_out(0, 4), a 3×3 area is set to overlap the above area, and four R signal values included in the 3×3 area are summed up. This also applies to Gr, Gb, and B.

This makes it possible to generate an output signal having the same number of pixels as that of the input signal. In this case, since the input signals of 3×3 pixels are used when calculating one pixel of the output signal, the pixel pitch increases by mixture reading by a factor of 3.

Note that the pixel binning method is not limited to the expressions (1). The following expressions (2) may be used instead of the expressions (1).

$$R\_out(x, y) = R(2x, 2y) + R(2x+2, 2y) + R(2x, 2y+2) + R(2x+2, 2y+2)$$

$$Gr\_out(x, y) = Gr(2x, 2y-1) + Gr(2x+2, 2y-1) + Gr(2x, 2y+1) + Gr(2x+2, 2y+1)$$

$$Gb\_out(x, y) = Gb(2x-1, 2y) + Gb(2x+1, 2y) + Gb(2x-1, 2y+2) + Gb(2x+1, 2y+1)$$

$$B\_out(x, y) = B(2x-1, 2y-1) + B(2x+1, 2y-1) + B(2x-1, 2y+1) + B(2x+1, 2y+1) \quad (2)$$

The expressions (2) are described below with reference to FIG. 4B. When calculating the signal value R_out(0, 0), four R signal values R(0, 0), R(2, 0), R(0, 2), and R(2, 2) included in a 3×3 area are summed up in the same manner as in FIG. 4A. In FIG. 4B, however, a 3×3 area is set so as not to overlap the above 3×3 area when calculating the signal value R_out(0, 4). Specifically, the signal values R(0, 4), R(2, 4), R(0, 6), and R(2, 6) are summed up when calculating the signal value R_out(0, 2). This also applies to Gr, Gb, and B.

This makes it possible to generate an output signal having a number of pixels smaller than that of the input signal (i.e., 2×2 pixels are generated from 4×4 pixels). Note that the pixel pitch increases by mixture reading by a factor of 3 in the same manner as in FIG. 4A.

The read mode control section 270 synthesizes the resulting signals in the same format as that of the analog signal output from the imaging element 250, and outputs the resulting signal.

The relationship between the read mode and the depth of field is described below.

Figure 5:
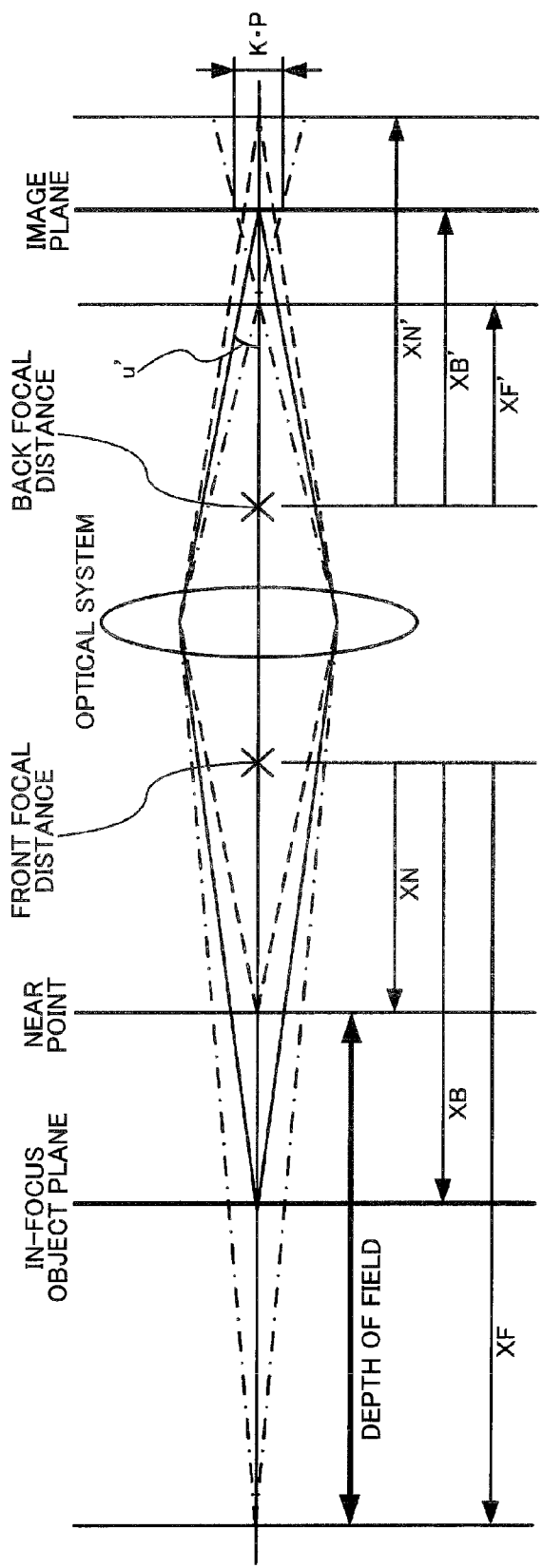
FIG. 5 is a view illustrative of the depth of field.

The depth of field is described in detail below with reference to FIG. 5. In FIG. 5, a right arrow indicates a vector having a positive value, and a left arrow indicates a vector having a negative value. When an imaging element having a pixel pitch (vertical and horizontal dimensions of one pixel) of P is disposed at a distance XB' from the back focal distance of the optical system, the position (in-focus object plane) of the object where the optical system has the best imaging performance in the image plane of the imaging element is the position at a distance XB from the front focal distance of the optical system. The distance XB is calculated by the following Newton's equation (3). Note that f is the focal length of the optical system.

$$XB*XB' = -f^2 \quad (3)$$

When the object is moved to the position at a distance XN from the front focal distance of the optical system, the image plane position XN' moves from the image plane in the direction opposite to the optical system. However, when the diameter of the circle of confusion in the image plane is smaller than the resolution K·P (where, K is a coefficient determined by the filter array and the interpolation process) of the imaging apparatus, the object positioned at the distance XN from the front focal distance of the optical system is considered to be in focus. A range in which the diameter of the circle of confusion in the image plane is equal to or smaller than K·P is defined as the near point-side depth of field, and the position of the object where the diameter of the circle of confusion coincides with K·P is hereinafter referred to as "near point". The position of the near point is hereinafter expressed by the position at the distance XN from the front focal distance. The above definition is similarly applied to the far point-side depth of field. The far point-side position of the object where the diameter of the circle of confusion coincides with K·P is hereinafter referred to as "far point". The position of the far point is hereinafter expressed by the position at the distance XF from the front focal distance.

The diameter of the circle of confusion in the image plane when the object is positioned at the near point is approximated by the following expression (4) using the numerical aperture NA" (=sin(u')) (where, u' is the angle formed by the optical axis and a beam that enters the image plane shown in FIG. 5) of the optical system.

$$\text{Diameter of circle of confusion} = 2(XN' - XB')*NA' \quad (4)$$

Since the diameter of the circle of confusion coincides with K·P at the near point, the following expression is obtained.

$$2(XN' - XB')*NA' = K*P \quad (5)$$

Transforming the expression (5) using the following expression (6) (i.e., relational expression of the F-number and the numerical aperture) yields the following expression (7). Note that F is the F-number of the optical system.

$$F = \tfrac{1}{2}NA' \quad (6)$$

$$XN' - XB = K*P*F \quad (7)$$

Transforming the expression (7) using Newton's equation (3) yields the following expression (8) (i.e., relational expression of the near point-side depth of field).

$$\frac{1}{XB} - \frac{1}{XN} = \frac{K \cdot P \cdot F}{f^2} \quad (8)$$

The relational expression of the far point-side depth of field calculated in the same manner as the near point-side depth of field is shown by the following expression (9).

$$\frac{1}{XF} - \frac{1}{XB} = \frac{K \cdot P \cdot F}{f^2} \quad (9)$$

The expressions (7) and (8) can be transformed into the following expressions (10) and (11). The position XN of the near point and the position XF of the far point can be calculated using the expressions (10) and (11).

$$XN = \frac{f^2 \cdot XB}{f^2 - KPF \cdot XB} \quad (10)$$

$$XF = \frac{f^2 \cdot XB}{f^2 + KPF \cdot XB} \quad (11)$$

Figure 6:
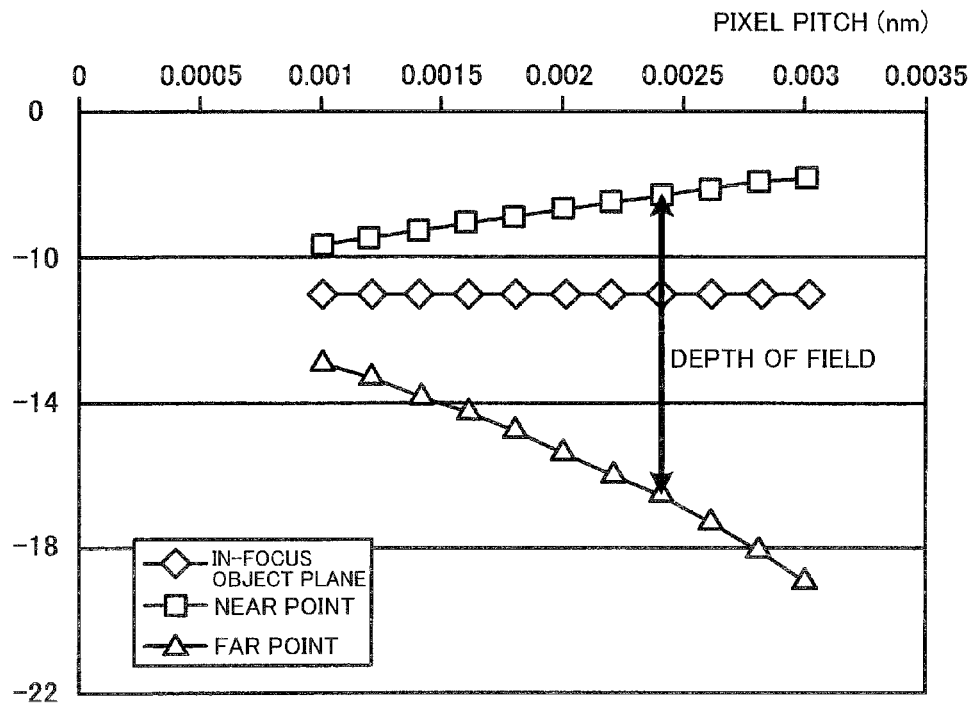
FIG. 6 shows the relationship between the pixel pitch and the depth of field when the in-focus object plane is fixed.

FIG. 6 shows an example of the relationship between the depth of field and the pixel pitch calculated using the expressions (10) and (11). The vertical axis indicates the in-focus object plane, the near point, and the far point with respect to the front focal distance. The range between the near point and the far point is the depth of field. The horizontal axis indicates the pixel pitch. When the focal length f, the F-number F, the coefficient K, and the in-focus object plane distance XB of the optical system are constant, the near point and the far point approach (i.e., the depth of field decreases) the in-focus object plane as the pixel pitch P decreases.

In the all-pixel read mode, the pixel pitch (vertical and horizontal dimensions of one pixel) is P. In the pixel binning read mode, the pixel pitch is P×3 when four pixels that are mixed are virtually considered to be one pixel. Therefore, the pixel pitch virtually increases in the pixel binning read mode, so that the depth of field increases.

Note that the pixel binning method in the pixel binning read mode is not limited to the above method. A similar effect can be achieved when using another pixel binning method.

The relationship between the in-focus object plane and the depth of field is described below.

Figure 7:
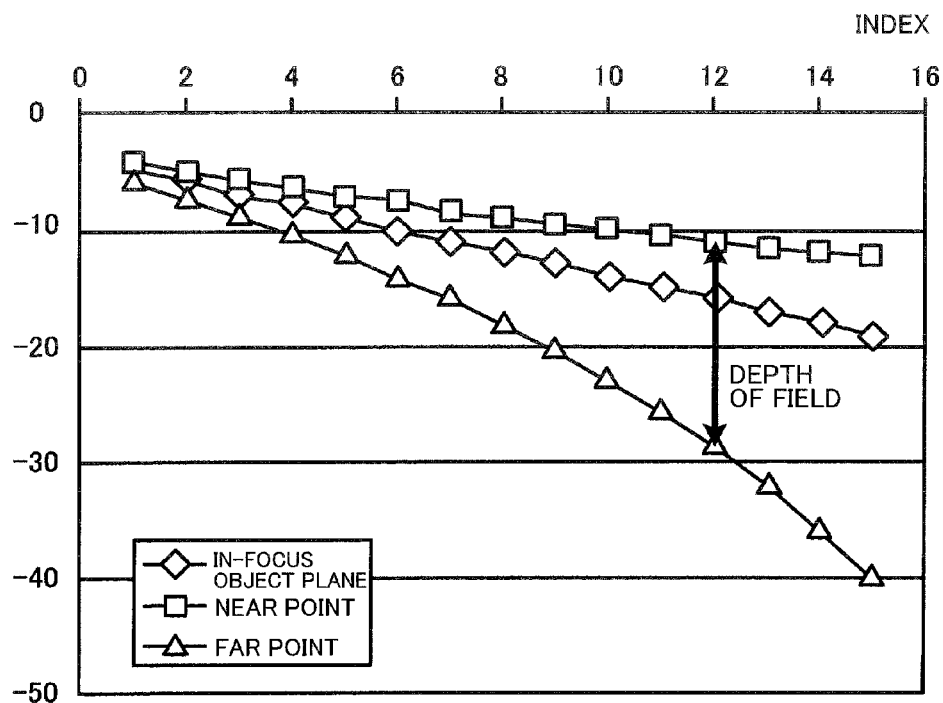
FIG. 7 shows the relationship between the pixel pitch and the depth of field when the in-focus object plane is variable.

FIG. 7 shows an example of the relationship between the in-focus object plane and the depth of field calculated using the expressions (10) and (11). The vertical axis indicates the in-focus object plane, the near point, and the far point with respect to the front focal distance. The range between the near point and the far point is the depth of field. The horizontal axis indicates an index value added to each in-focus object plane. When the focal length f, the F-number F, the coefficient K, and the pixel pitch P of the optical system are constant, the near point and the far point approach (i.e., the depth of field decreases) the front focal distance as the in-focus object plane distance XB approaches the front focal distance.

The relationship between the read mode and the in-focus object plane in each observation mode is described below with reference to FIG. 8.

When a doctor observes a subject using the endoscope system, the doctor observes a wide range while moving the imaging section 200 inside a body cavity. When the doctor has found a attention area suspected to be a lesion, the doctor positions the imaging section 200 near the attention area, and closely observes the blood vessels, the surface structure, and the like. Therefore, it is important that both the close object and the distant object be in focus in the distant observation mode used to observe a wide range. In the close observation mode used to closely observe the attention area, since the observation target object is limited, it is important to implement high resolving power even if the depth of field is narrow.

In the endoscope system according to this embodiment, when the distant observation mode has been selected, the observation mode setting section 340 determines that the observation mode is the distant observation mode based on a control signal from the external IN section 500, and outputs the observation mode information to the control section 330. In this case, the control section 330 outputs a read mode control signal to the read mode control section 270 so that the read mode control section 270 selects the pixel binning read mode. The control section 330 outputs a given focus control signal to the lens driver section 260 so that the lens driver section 260 moves the in-focus object plane to a predetermined position. A wide depth of field shown in FIG. 8A can thus be achieved.

When the close observation mode has been selected, the observation mode setting section 340 determines that the observation mode is the close observation mode based on a control signal from the external I/F section 500, and outputs the observation mode information to the control section 330. In this case, the control section 330 outputs the read mode control signal to the read mode control section 270 so that the read mode control section 270 selects the all-pixel read mode. If the in-focus object plane is the same position as that in the pixel binning read mode, the near point and the far point approach the in-focus object plane so that the depth of field decreases (see FIG. 8B). As a result, the attention area is positioned outside the depth of field when moving the imaging section 200 close to the attention area, so that sufficient resolving power cannot be obtained. Therefore, when the close observation mode has been selected, the control section 330 also outputs the given focus control signal to the lens driver section 260 so that the lens driver section 260 moves the in-focus object plane to a predetermined position closer to the imaging section 200 than the position in the distant observation mode. This makes it possible to move the depth of field closer to the imaging section 200 (see FIG. 8C), so that sufficient resolving power can be obtained even when the imaging section 200 is positioned close to the attention area.

According to this embodiment, the imaging apparatus includes the imaging section 200, the observation mode setting section 340 that sets the observation mode, and the control section 330 that controls the image read mode from the imaging section 200 and the in-focus object plane of the imaging section 200 based on the observation mode set by the observation mode setting section 340.

This makes it possible to control the image read mode and the in-focus object plane based on the set observation mode. Therefore, a plurality of observation modes that differ in characteristics can be set, so that the read mode and the in-focus object plane can be appropriately controlled depending on the photographic conditions in each observation mode.

It is also possible to appropriately set the in-focus distance by controlling both the image read mode and the in-focus object plane depending on the observation mode. As shown in FIG. 7, the depth of field decreases as the in-focus object plane approaches the imaging apparatus, and increases as the in-focus object plane moves away from the imaging apparatus. Therefore, when using a mode in which the depth of field is increased by controlling the read mode, a wider depth of field can be obtained or the wide depth of field due to the read mode can be maintained by also controlling the in-focus object plane to move away from the imaging apparatus. Specifically, a mode that pursues the depth of field can be implemented.

When performing a normal read operation by controlling the read mode, a range near the imaging apparatus cannot be brought into focus if the depth of field is relatively narrow, and the in-focus object plane is distant from the imaging apparatus. Therefore, a range near the imaging apparatus is covered by moving the in-focus object plane closer to the imaging apparatus. Since a normal read operation is performed in this mode, a high-resolution image can be obtained since the depth of field is narrow. Specifically, a mode that pursues the resolution can be implemented.

The control section 330 sets the image read mode to the pixel binning read mode in the distant observation mode, and sets the image read mode to the all-pixel read mode in the close observation mode. In the close observation mode, the control section 330 causes the in-focus object plane to move closer to the imaging section 200 as compared with the distant observation mode.

In the distant observation mode, deep focusing is implemented by setting the image read mode to the pixel binning read mode, and setting the in-focus object plane to be relatively distant from the imaging section 200. In the close observation mode, a high-resolution image can be acquired by setting the image read mode to the all-pixel read mode, and an image in which the object is in focus can be acquired by setting the in-focus object plane to be close to the imaging section 200. The term "deep focusing" refers to a photographic technique that achieves a wide in-focus range by photographing an object with a wide depth of field.

The control section 330 variably sets the depth of field by performing the pixel binning read process, even if the in-focus object plane is fixed.

This makes it possible to variably set the depth of field using the pixel binning read process. The depth of field changes depending on the in-focus object plane. The above expression "variably sets the depth of field" means that the depth of field can be changed without taking account of the effect of the in-focus object plane (i.e., even if the in-focus object plane is fixed). Note that the depth of field may be variably set by a method other than the pixel binning read process insofar as the size of the circle of confusion can be increased by handling a plurality of pixels as one pixel, for example. When handling 3×3 pixels as one pixel, for example, the pixel binning read process calculates the sum of the nine pixels or only necessary pixels. Note that the pixel value of a given pixel may be used as the output value.

When the depth of field specified by the permissible circle of confusion corresponding to the pixel pitch of the imaging element 250 is referred to as D1, and the depth of field in the distant observation mode is referred to as D2, the relationship "D2>D1" is satisfied.

Therefore, a depth of field wider than the depth of field determined by the pixel pitch of the imaging element can be implemented in the distant observation mode.

The depth of field D2 is specified by the permissible circle of confusion corresponding to the pixel pitch when a plurality of pixels are handled as one pixel.

This makes it possible to implement a depth of field that satisfies the relationship "D2>D1" by handling a plurality of pixels as one pixel. Specifically, the pixel pitch is increased by decreasing the resolution. Therefore, the size of the permissible circle of confusion increases, so that the depth of field can be increased. For example, when handling 3×3 pixels as one pixel, the pixel pitch increases by a factor of 3, as described above with reference to FIGS. 4A and 4B. The depth of field can be increased by increasing the pixel pitch (see FIG. 6).

The imaging apparatus may include an input reception section that receives instructions from the user. The observation mode setting section 340 may set the observation mode based on the instructions from the user.

This makes it possible to set the observation mode (e.g., distant observation mode and close observation mode) based on the instructions from the user. Since the mode is set in accordance with the user's intention, the possibility that the mode is erroneously set can be reduced.

The imaging apparatus according to this embodiment may include the imaging section 200, the observation mode setting section 340, and the control section 330. When the observation mode is a first observation mode, the depth of field is variably controlled even if the in-focus object plane is the same. When the observation mode is a second observation mode, the in-focus object plane may be moved closer to the imaging section 200 as compared with the first observation mode. The first observation mode may be the distant observation mode, and the second observation mode may be the close observation mode.

This makes it possible to control the depth of field and the in-focus object plane based on the set observation mode. The depth of field also changes depending on the in-focus object plane. In this embodiment, the depth of field is controlled based on a factor other than the movement of the in-focus object plane. Specifically, the depth of field is variably controlled in the first observation mode, and the in-focus object plane is moved closer to the imaging section 200 in the second observation mode. The first observation mode may be the distant observation mode in which a wide range is observed as compared with the second mode, and the second observation mode may be the close observation mode in which the imaging section 200 faces the object.

The control section 330 may decrease the depth of field in the close observation mode, and increase the depth of field in the distant observation mode.

This makes it possible to implement deep focusing in the distant observation mode. In the close observation mode, the depth of field may be narrow since it is assumed that the imaging section 200 faces the object. Therefore, disadvantages (e.g., the image darkens due to a decrease in aperture, or the resolution decreases) due to deep focusing can be prevented.

The imaging apparatus according to this embodiment may be an endoscope system that includes the imaging section 200, the observation mode setting section 340 that sets the observation mode, and the control section 330 that controls the image read mode from the imaging section 200 and the in-focus object plane of the imaging section 200 based on the observation mode set by the observation mode setting section 340.

This makes it possible to implement an endoscope system that can control the image read mode and the in-focus object plane based on the observation mode. Since the endoscope system can be set to a plurality of modes, an endoscope system that facilitates diagnosis by a doctor can be implemented.

The imaging apparatus according to this embodiment may be an endoscope system that includes the imaging section 200, the observation mode setting section 340, and the control section 330 that controls the depth of field and the in-focus object plane based on the observation mode.

This makes it possible to implement an endoscope system that can control the depth of field and the in-focus object plane based on the set observation mode.

In such an endoscope system, the depth of field is narrow in the close observation mode, and is wide in the distant observation mode in the same manner as in the imaging apparatus. The endoscope system may also be configured so that the depth of field is variably set by the pixel binning read process, the relationship "D2>D1" is satisfied, and the depth of field D2 is specified by the permissible circle of confusion corresponding to the pixel pitch when a plurality of pixels are handled as one pixel.

This embodiment may also be applied to a method of controlling an imaging apparatus including setting an observation mode, controlling an image read mode and a in-focus object plane based on the observation mode, and controlling the imaging apparatus so that the imaging apparatus images an object based on control of the read mode and the in-focus object plane.

This makes it possible to implement a method of controlling an imaging apparatus that can control the image read mode and the in-focus object plane based on the observation mode.

3. Second Embodiment

An endoscope system according to a second embodiment of the invention is described below with reference to FIG. 9. The endoscope system according to this embodiment includes a light source section 100, an imaging section 200, a processing section 300, a display section 400, and an external I/F section 500. The configuration other than the light source section 100, the imaging section 200, and the processing section 300 is the same as that of the first embodiment.

The light source section 100 includes a white light source 110 that emits (generates) white light, a condenser lens 120 that focuses white light on a light guide fiber 210, a rotary filter 130 that extracts light having a given wavelength band from white light, and a filter driver section 140 that drives the rotary filter.

Figure 10:
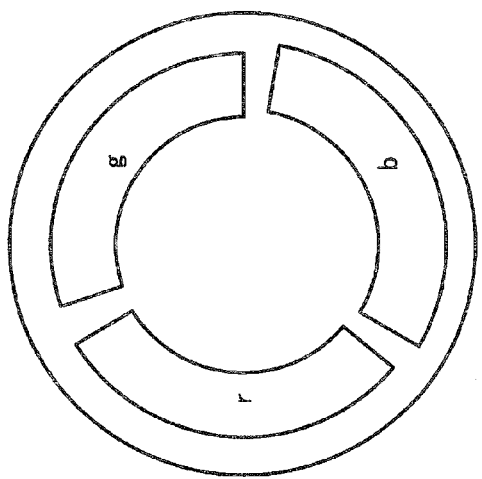
FIG. 10 shows an example of a rotary filter.
Figure 11:
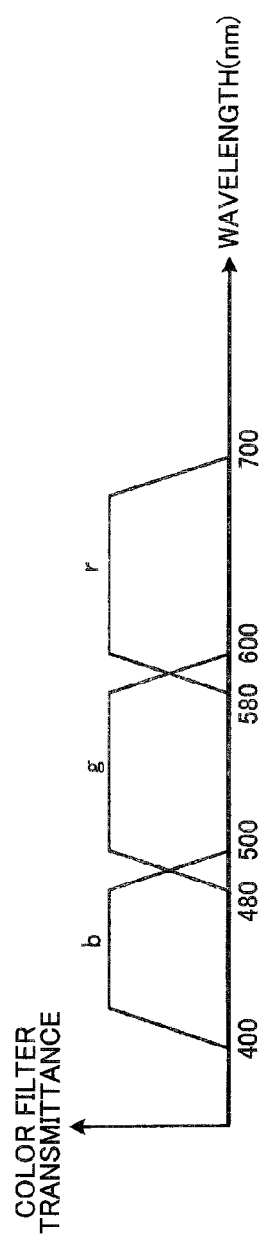
FIG. 11 shows the spectral characteristics of filters r, g, and b.

As shown in FIG. 10, the rotary filter 130 includes three color filters r, g, and b, for example. FIG. 11 shows an example of the spectral transmittance of each color filter. The filter driver section 140 causes illumination light to be applied to the observation target while sequentially switching the color filters r, g, and b by driving (rotating) the rotary filter 130 based on a signal output from a control section 330 described later. The control section 330 outputs information about the color filter r, g, or b disposed in the optical path to an image processing section 320 described later as a trigger signal.

The imaging section 200 is formed to be elongated and flexible (i.e., can be curved) so that the imaging section 200 can be inserted into a body cavity or the like. The imaging section 200 includes the light guide fiber 210 that guides light focused by the light source section, an illumination lens 220 that diffuses light guided to the end of the imaging section 200 by the light guide fiber 210 so that the diffused light is applied to an observation target, an objective lens 230 that focuses light reflected from the observation target, a focus adjustment lens 240 that adjusts the in-focus object plane, an imaging element 250 that detects focused reflected light, a read mode control section 270 that controls a read mode when reading a signal from the imaging element, and outputs an analog signal, and a lens driver section 260 that drives the focus adjustment lens 240. Note that various modifications may be made, such as omitting some of the elements or adding other elements.

The lens driver section 260 is a stepping motor, for example. The lens driver section 260 is connected to the focus adjustment lens 240. The lens driver section 260 adjusts the in-focus object plane by changing the position of the focus adjustment lens. The imaging element 250 is a monochrome imaging element having a pixel pitch P. The details of the read mode control section 270 are described later.

The processing section 300 includes an AD conversion section 310, an image processing section 320, a control section 330, and an observation mode setting section 340. Note that various modifications may be made, such as omitting some of the elements or adding other elements.

The AD conversion section 310 converts an analog signal output from the read mode control section 270 into a digital signal, and outputs the digital signal. The image processing section 320 includes three storage areas corresponding to the color filters r, g, and b. The image processing section 320 identifies the type of color filter corresponding to the image output from the AD conversion section 310 based on the trigger signal output from the control section 330, and updates the image stored in the corresponding storage area. The image processing section 320 performs an image process (e.g., white balance process, color conversion process, and grayscale transformation process) on the images stored in the three storage areas, and outputs the image to the display section 400.

The observation mode setting section 340 sets the observation mode based on a control signal input from the external I/F section 500, and outputs observation mode information to the control section 330. The control section 330 controls the lens driver section 260 and the read mode control section 270 based on the received observation mode information.

The details of the read mode control section 270 are described below. The read mode control section 270 receives a 1-channel analog signal from each pixel of the imaging element, and outputs a 1-channel analog signal. The read mode control section 270 switches the read mode between an all-pixel read mode and a pixel binning read mode based on a control signal output from the control section 330. When the all-pixel read mode has been selected, the read mode control section 270 directly outputs the input 1-channel analog signal.

When the pixel binning read mode has been selected, the read mode control section 270 sums up the signal values of the input 1-channel analog signals corresponding to 2×2 pixels that are adjacent in the horizontal direction and the vertical direction. The signal values of 4×4 pixels (see FIG. 12A) input to the read mode control section 270 from the imaging element 250 are summed up according to the following expression (12) to obtain the signal values of 2×2 pixels. Note that P(x, y) is the input signal value, and P_out(x, y) and Gr_out are signal values obtained by summing up the input signal values.

$$P\_out(x, y) = P(2x, 2y) + P(2x+1, 2y) + P(2x, 2y+1) + P(2x+1, 2y+1) \quad (12)$$

Figure 12A:
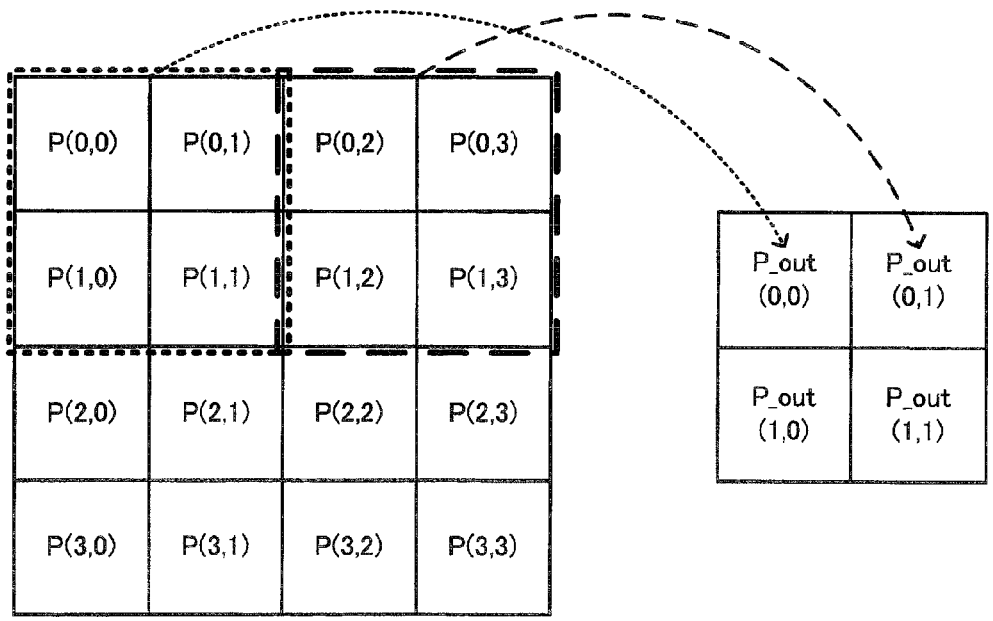
FIGS. 12A and 12B are views illustrative of an image when performing a pixel binning read process.

The expression (12) is described below with reference to FIG. 12A. For example, when calculating the signal value P_out(0, 0), four signal values P(0, 0), P(1, 0), P(0, 1), and P(1, 1) included in a 2×2 area are summed up. When calculating the signal value P_out(0, 2), a 2×2 area is set so as not to overlap the above area, and four R signal values included in the 2×2 area are summed up.

This makes it possible to generate an output signal having a number of pixels smaller than that of the input signal (i.e., 2×2 pixels are generated from 4×4 pixels). In this case, since the input signals of 2×2 pixels are used when calculating one pixel of the output signal, the pixel pitch increases by mixture reading by a factor of 2.

Note that the pixel binning method is not limited to the expression (12). The following expression (13) may be used instead of the expression (12).

$$P\_out(x, y) = P(x, y) + P(x+1, y) + P(x, y+1) + P(x+1, y+1) \quad (13)$$

Figure 12B:
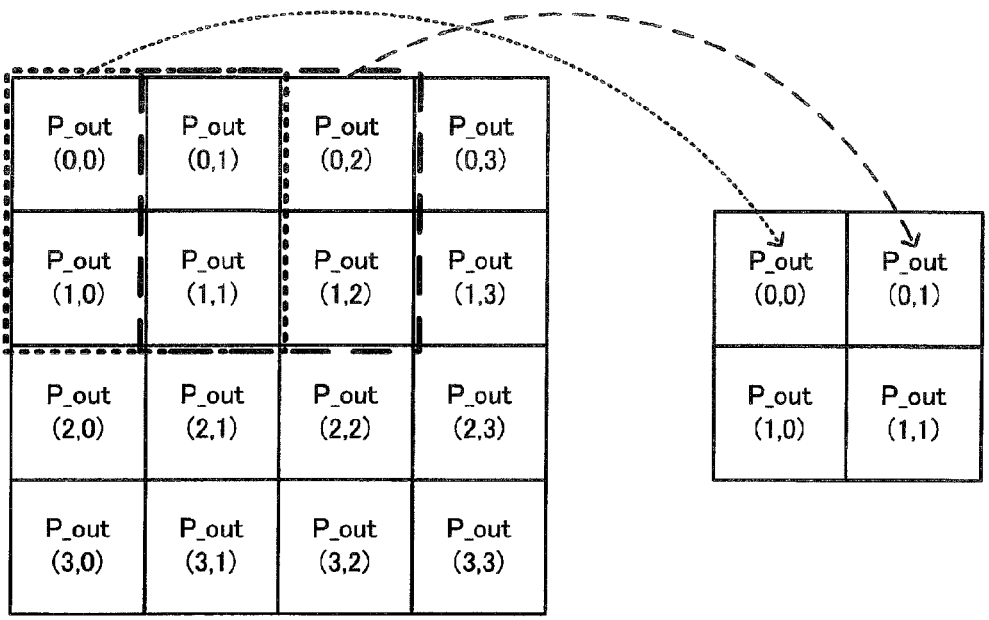

The expression (13) is described below with reference to FIG. 12B. When calculating the signal value P_out(0, 0), four signal values P(0, 0), P(1, 0), P(0, 1), and P(1, 1) included in a 2×2 area are summed up in the same manner as in FIG. 12A. In FIG. 12B, however, a 2×2 area is set to overlap the above 2×2 area when calculating the signal value P_out(0, 1). Specifically, the signal values P(0, 1), P(1, 1), P(0, 2), and PR(1, 2) are summed up when calculating the signal value P_out(0, 1).

This makes it possible to generate an output signal having a number of pixels smaller than that of the input signal (i.e., 2×2 pixels are generated from 4×4 pixels). Note that the pixel pitch increases by mixture reading by a factor of 2 in the same manner as in FIG. 12A.

The read mode control section 270 then outputs the 1-channel analog signal obtained by summing up the signal values.

In the all-pixel read mode, the pixel pitch (vertical and horizontal dimensions of one pixel) is P. In the pixel binning read mode, the pixel pitch is P×2 when four pixels that are mixed are virtually considered to be one pixel. Therefore, the pixel pitch virtually increases in the pixel binning read mode, so that the depth of field increases.

Note that the pixel binning method in the pixel binning read mode is not limited to the above method. A similar effect can be achieved when using another pixel binning method.

The relationship between the read mode and the in-focus object plane in each observation mode is described below. The basic operation is the same as that of the first embodiment.

In the endoscope system according to this embodiment, when the distant observation mode has been selected, the observation mode setting section 340 determines that the observation mode is the distant observation mode based on a control signal from the external I/F section 500, and outputs the observation mode information to the control section 330. In this case, the control section 330 outputs a read mode control signal to the read mode control section 270 so that the read mode control section 270 selects the pixel binning read mode. The control section 330 outputs a given focus control signal to the lens driver section 260 so that the lens driver section 260 moves the in-focus object plane to a predetermined position. A wide depth of field shown in FIG. 8A can thus be achieved.

When the close observation mode has been selected, the observation mode setting section 340 determines that the observation mode is the close observation mode based on a control signal from the external I/F section 500, and outputs the observation mode information to the control section 330. In this case, the control section 330 outputs the read mode control signal to the read mode control section 270 so that the read mode control section 270 selects the all-pixel read mode. The control section 330 outputs a given focus control signal to the lens driver section 260 so that the lens driver section 260 moves the in-focus object plane to a predetermined position. This makes it possible to move the depth of field closer to the imaging section 200 (see FIG. 8C), so that sufficient resolving power can be obtained even when the imaging section 200 is positioned close to the attention area.

4. Third Embodiment

Figure 13:
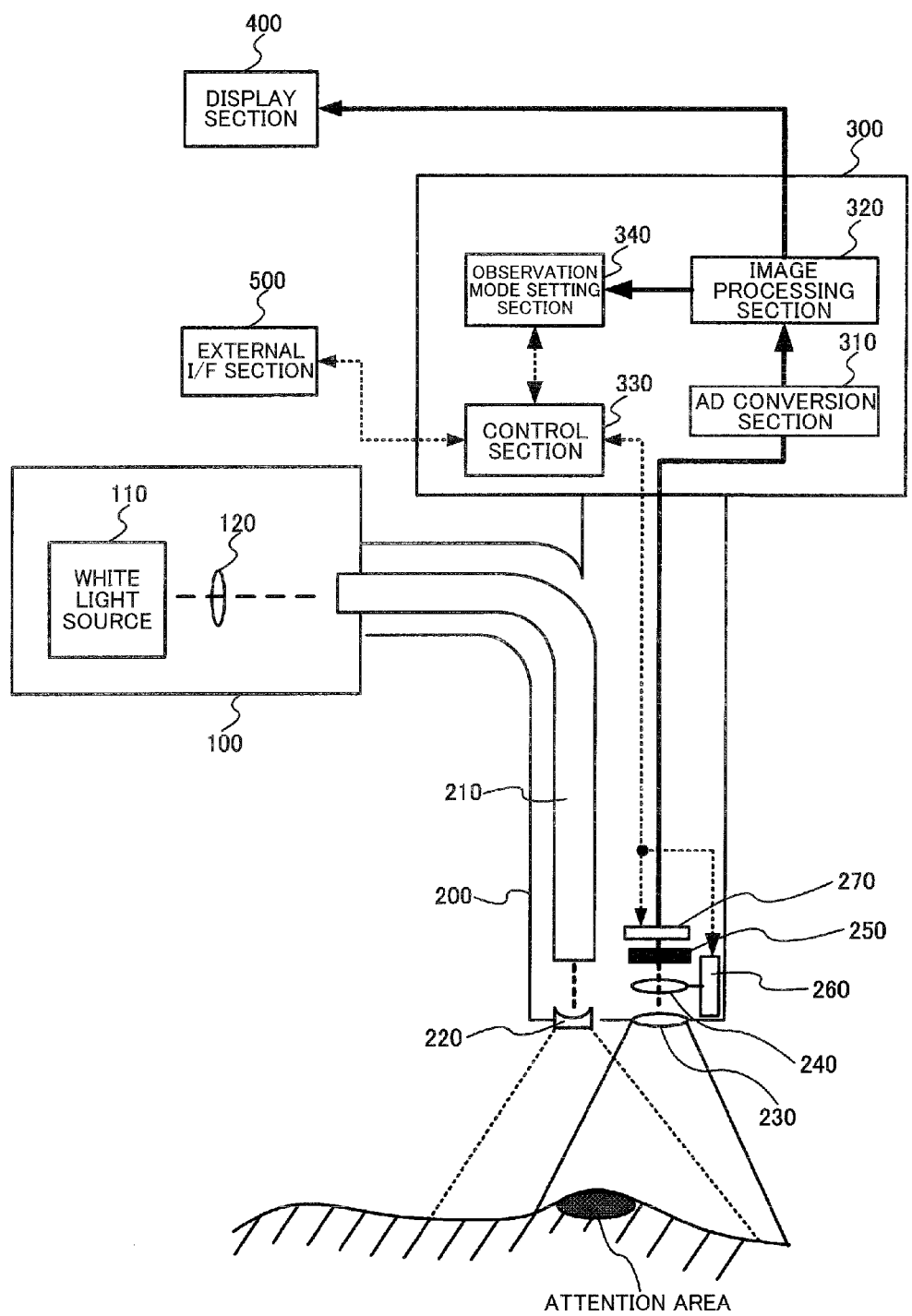
FIG. 13 shows another system configuration example according to one embodiment of the invention.

An endoscope system according to a third embodiment of the invention is described below with reference to FIG. 13. The endoscope system according to this embodiment includes a light source section 100, an imaging section 200, a processing section 300, a display section 400, and an external I/F section 500. The configuration other than the processing section 300 is the same as that of the first embodiment.

The processing section 300 according to this embodiment includes an AD conversion section 310, an image processing section 320, a control section 330, and an observation mode setting section 340. Note that various modifications may be made, such as omitting some of the elements or adding other elements.

The AD conversion section 310 converts an analog signal output from the read mode control section 270 into a digital signal, and outputs the digital signal. The image processing section 320 performs an image process (e.g., white balance process, interpolation process, color conversion process, and grayscale transformation process) on the digital signal output from the AD conversion section 310, and outputs an image to the display section 400 and the observation mode setting section 340. The observation mode setting section 340 calculates a feature quantity from the image output from the image processing section 320, determines an observation mode based on the feature quantity, and outputs observation mode information to the control section 330. The control section 330 controls the lens driver section 260 and the read mode control section 270 based on the received observation mode information.

Figure 14:
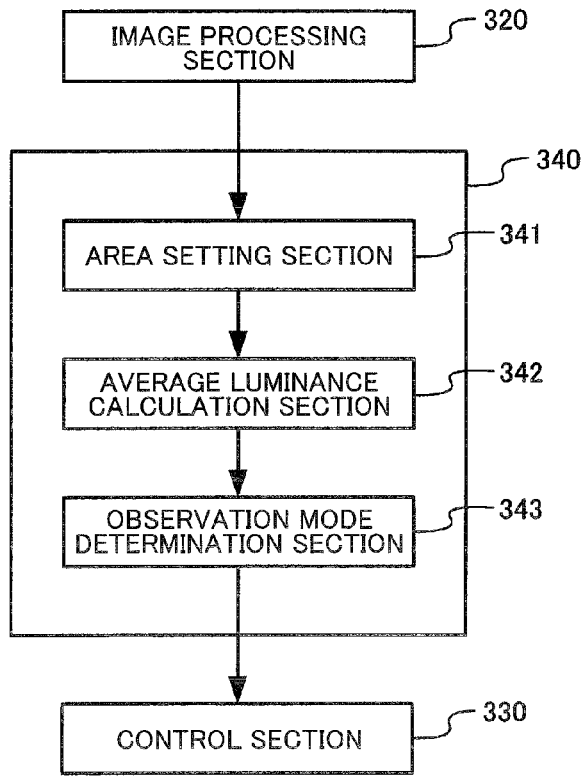
FIG. 14 shows a configuration example of the observation mode setting section.

The details of the observation mode setting section 340 according to this embodiment are described below. FIG. 14 is a block diagram showing an example of the observation mode setting section 340. The observation mode setting section 340 includes an area setting section 341, an average luminance calculation section 342, and an observation mode determination section 343.

The area setting section 341 sets an area 1 and an area 2 to the image output from the image processing section 320 (see FIG. 15). In this example, an area for which a distance r from the center of the image satisfies the following expression (14) is set as the area 1, and an area for which the distance r from the center of the image satisfies the following expression (15) is set as the area 2.

$$0 \leq r \leq r0 \tag{14}$$

$$r0 < r \tag{15}$$

The average luminance calculation section 342 calculates the average luminance L1 of the area 1 and the average luminance L2 of the area 2. The observation mode determination section 343 determines the observation mode from the relationship between the average luminance L1 and the average luminance L2 calculated by the average luminance calculation section 342.

Figure 15A:
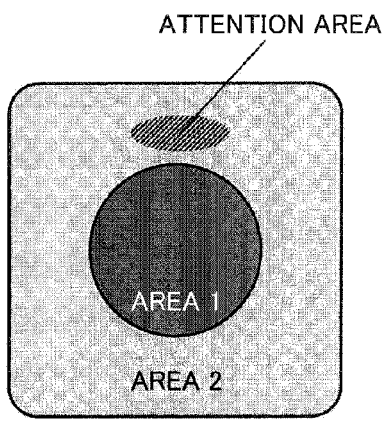
FIG. 15A is a view illustrative of a case where a peripheral area is brighter than a center area.
Figure 15B:
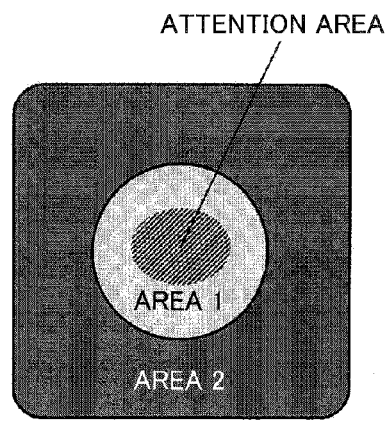
FIG. 15B is a view illustrative of a case where a center area is brighter than a peripheral area.

The relationship between the average luminance L1 and the average luminance L2 in each observation mode is described below with reference to FIGS. 15A, 15B, and 16. A bold line in FIG. 16 indicates the shape of a living body (object) and a broken line indicates the viewing angle of the imaging section 200. A range that almost coincides with the viewing angle is illuminated by an illumination section (not shown) provided near the imaging section.

As shown in FIG. 16A, since the imaging section 200 moves through a hollow tubular object in the distant observation mode, an object positioned around the center of the image is distant from the imaging section 200 as compared with the object positioned in the peripheral area of the image. Therefore, an images in which the area 2 (peripheral area) is brighter than the area 1 (center area) is obtained (see FIG. 15A). Therefore, the observation mode determination section 343 determines that the observation mode is the distant observation mode when the average luminance L2 is higher than the average luminance L1, and outputs the observation mode information to the control section 330.

In the close observation mode, the imaging section 200 faces the wall of the object, and is adjusted so that the attention area is positioned around the center of the image (see FIG. 16B). In this case, since the distance between the imaging section and the object changes to only a small extent in the center area and the peripheral area of the image, an image in which the center area is brighter than the peripheral area is normally obtained due to the intensity distribution of illumination light, mechanical vignetting of the optical system, and the like (see FIG. 15B). Therefore, the observation mode determination section 343 determines that the observation mode is the close observation mode when the average luminance L1 is higher than the average luminance L2, and outputs the observation mode information to the control section 330.

The control section 330 controls the lens driver section 260 and the read mode control section 270 based on the received observation mode information in the same manner as in the first embodiment.

Although this embodiment utilizes the luminance of the image as the feature quantity, the observation mode may also be determined using a feature quantity other than the luminance. For example, the observation mode determination section 343 may perform a known frequency decomposition process on the image input from the display image generation section, and may determine whether the observation mode is the distant observation mode or the close observation mode based on the frequency characteristics of the image. Specifically, the observation mode determination section 343 sets the observation mode to the distant observation mode when the amount of high-frequency components is larger than the amount of low-frequency components, and sets the observation mode to the close observation mode when the amount of low-frequency components is larger than the amount of high-frequency components.

According to this embodiment, the observation mode setting section 340 sets the observation mode based on the feature quantity of the image.

This makes it possible to set the observation mode based on the feature quantity of the image even if instructions have not issued by the user. Therefore, it is unnecessary to reset the observation mode even if the observation state has changed, so that convenience to the user increases.

The feature quantity of the image may be luminance information about the image. Specifically, the average luminance L1 of the center area of the image and the average luminance L2 of the peripheral area of the image may be calculated, the observation mode may be set to the close observation mode when the average luminance L1 is higher than the average luminance L2, and may be set to the distant observation mode when the average luminance L2 is higher than the average luminance L1.

This makes it possible to set the observation mode based on the luminance information about the image. Since it is assumed that the imaging section 200 faces the object (see FIG. 16B) when the average luminance L1 is higher than the average luminance L2, it may be determined that the attention area is positioned close to the imaging section 200, and the close observation mode is suitable. Since it is assumed that the imaging section 200 is positioned inside the hollow tubular object (see FIG. 16A) when the average luminance L2 is higher than the average luminance L1, it may be determined that the attention area is not necessarily positioned close to the imaging section 200, and the distant observation mode with a wide depth of field is suitable.

The feature quantity of the image may be the spatial frequency characteristics of the image. Specifically, the observation mode may be set to the close observation mode when the amount of low-frequency components is larger than the amount of high-frequency components, and may be set to the distant observation mode when the amount of high-frequency components is larger than the amount of low-frequency components.

This makes it possible to set the observation mode based on the spatial frequency characteristics of the image. Since it is assumed that the object occupies a large area of the image when the amount of low-frequency components is larger than the amount of high-frequency components, it may be determined that the attention area is positioned close to the imaging section 200, and the close observation mode is suitable. Since it is assumed that the object occupies a small area of the image when the amount of high-frequency components is larger than the amount of low-frequency components, it may be determined that the distant observation mode is suitable.

5. Fourth Embodiment

Figure 17:
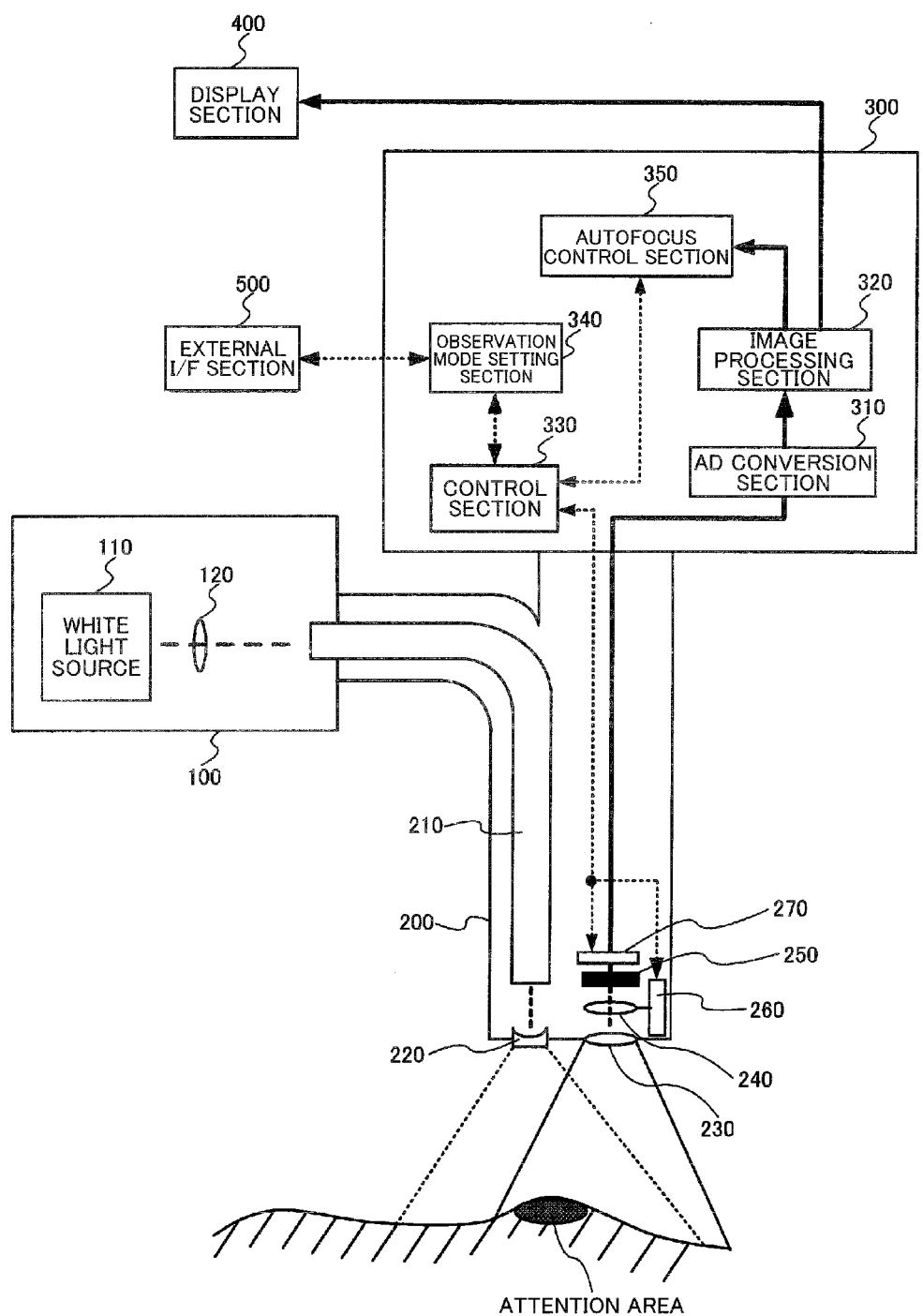
FIG. 17 shows yet another system configuration example according to one embodiment of the invention.

An endoscope system according to a fourth embodiment of the invention is described below with reference to FIG. 17. The endoscope system according to this embodiment includes a light source section 100, an imaging section 200, a processing section 300, a display section 400, and an external I/F section 500. The configuration other than the processing section 300 is the same as that of the first embodiment.

The processing section 300 according to this embodiment includes an AD conversion section 310, an image processing section 320, a control section 330, an observation mode setting section 340, and an autofocus control section 350. Note that various modifications may be made, such as omitting some of the elements or adding other elements.

The AD conversion section 310 converts an analog signal output from the read mode control section 270 into a digital signal, and outputs the digital signal. The image processing section 320 performs an image process (e.g., white balance process, interpolation process, color conversion process, and grayscale transformation process) on the digital signal output from the AD conversion section 310, and outputs an image to the display section 400 and the autofocus control section 350. The autofocus control section 350 generates a focus control signal that controls the in-focus object plane so that the object coincides with the in-focus object plane distance XB by a known method using the image output from the image processing section 320, and outputs the focus control signal to the control section 330. The observation mode setting section 340 determines the observation mode based on a control signal input from the external I/F section 500, and outputs observation mode information to the control section 330. The control section 330 controls the lens driver section 260 and the read mode control section 270 based on the observation mode information received from the observation mode setting section 340 and the focus control signal received from the autofocus control section 350.

The relationship between the read mode and the in-focus object plane in each observation mode is described below. In the endoscope system according to this embodiment, when the distant observation mode has been selected, the observation mode setting section 340 determines that the observation mode is the distant observation mode based on a control signal from the external I/F section 500, and outputs the observation mode information to the control section 330. In this case, the control section 330 outputs a read mode control signal to the read mode control section 270 so that the read mode control section 270 selects the pixel binning read mode. The control section 330 outputs a given focus control signal to the lens driver section 260 so that the lens driver section 260 moves the in-focus object plane to a predetermined position. A wide depth of field shown in FIG. 8A can thus be achieved in the same manner as in the first embodiment.

When the close observation mode has been selected, the observation mode setting section 340 determines that the observation mode is the close observation mode based on a control signal from the external I/F section 500, and outputs the observation mode information to the control section 330. In this case, the control section 330 outputs the read mode control signal to the read mode control section 270 so that the read mode control section 270 selects the all-pixel read mode.

The depth of field decreases as the in-focus object plane distance XB approaches the imaging section 200, as described with reference to FIG. 7. Therefore, if the range of the depth of field is fixed in the close observation mode (see FIG. 8C), it may be difficult to operate the imaging section so that the attention area enters the range of the depth of field. In this embodiment, the control section 330 outputs the focus control signal received from the autofocus control section 350 to the lens driver section 260 so that the lens driver section 260 controls the in-focus object plane such that the object coincides with the in-focus object plane. This makes it possible to reliably allow the attention area to be within the range of the depth of field even when the imaging section 200 approaches the attention area, so that sufficient resolving power can be obtained.

The first to fourth embodiments have been described taking an example in which the pixel pitch is increased in the distant observation mode when reading a signal from the imaging element 250. Note that the invention is not limited thereto. For example, a signal may be normally read from the imaging element 250, and the image processing section 320 may increase the pixel pitch by the image process.

According to this embodiment, the control section 330 determines the in-focus object plane depending on the position of the object.

This makes it possible to arbitrarily change the in-focus object plane depending on the position of the object, differing from the first to third embodiments (i.e., the in-focus object plane is fixed). Specifically, an autofocus function can be implemented.

The control section 330 sets the image read mode to the pixel binning read mode in the distant observation mode, and sets the image read mode to the all-pixel read mode in the close observation mode. The control section 330 may set the in-focus object plane at a given position in the distant observation mode, and may control the in-focus object plane in the close observation mode depending on the position of the object.

This makes it possible to change the image read mode depending on the observation mode. Moreover, it is possible to fix the in-focus object plane in the distant observation mode, and control (autofocus) the in-focus object plane in the close observation mode depending on the position of the object.

The first to fourth embodiments according to the invention and the modifications thereof have been described above. Note that the invention is not limited to the first to fourth embodiments and the modifications thereof. Various modifications and variations may be made without departing from the scope of the invention. A plurality of elements of each of the first to fourth embodiments and the modifications thereof may be appropriately combined. For example, an arbitrary element may be omitted from the first to fourth embodiments and the modifications thereof. The elements described in connection with the first to fourth embodiments and the modifications thereof may be appropriately combined. Specifically, various modifications and applications are possible without materially departing from the novel teachings and advantages of the invention.

Any term cited with a different term having a broader meaning or the same meaning at least once in the specification and the drawings can be replaced by the different term in any place in the specification and the drawings.

What is claimed is:

1. An imaging apparatus comprising:
    an imaging section that images an object;
    an observation mode setting section that sets an observation mode when the imaging section images the object; and
    a control section that switches an image read mode from a plurality of read modes in which an image is read from the imaging section and controls an in-focus object plane of the imaging section based on the observation mode set by the observation mode setting section; wherein
    the control section switches the image read mode from a distant observation mode and close observation mode, the distant observation mode performs a pixel binning read process, and the close observation mode performs an all-pixel read process;
    the control section, in a close observation mode, controls the in-focus object plane of the imaging section so that the in-focus object plane of the imaging section in the close observation mode is closer to the imaging section than that in the distant observation mode;
    the control section variably sets a depth of field by performing the pixel binning read process even if the in-focus object plane of the imaging section is fixed;
    a depth of field D1 is specified by a permissible circle of confusion corresponding to a pixel pitch of an imaging element included in the imaging section;
    a depth of field D2 is a depth of field in the distant observation mode; and
    the depth of field D1 and the depth of field D2 satisfying the relationship D2>D1.

2. The imaging apparatus as defined in claim 1, wherein the depth of field D2 in the distant observation mode is specified by a permissible circle of confusion corresponding to a pixel pitch when handling a plurality of pixels as one pixel.

3. The imaging apparatus as defined in claim 1, further comprising:
    an input reception section that receives instructions from a user,
    wherein the observation mode setting section sets the observation mode based on instructions received from the user.

4. The imaging apparatus as defined in claim 1, wherein the observation mode setting section sets the observation mode based on a feature quantity of the image.

5. The imaging apparatus as defined in claim 4, wherein the feature quantity of the image is luminance information about the image.

6. The imaging apparatus as defined in claim 5, wherein:
    the observation mode setting section calculates an average luminance L1 of a center area of the image and an average luminance L2 of a peripheral area of the image, and
    the observation mode setting section sets the observation mode to a close observation mode when the average luminance L1 is higher than the average luminance L2, and sets the observation mode to a distant observation mode when the average luminance L2 is higher than the average luminance L1.

7. The imaging apparatus as defined in claim 4, wherein the feature quantity of the image is spatial frequency characteristics of the image.

8. The imaging apparatus as defined in claim 7, wherein:
    the observation mode setting section calculates the spatial frequency characteristics of the image, and
    the observation mode setting section sets the observation mode to the close observation mode when the amount of low-frequency components is larger than the amount of high-frequency components, and sets the observation mode to the distant observation mode when the amount of high-frequency components is larger than the amount of low-frequency components.

9. The imaging apparatus as defined in claim 1, wherein the control section determines the in-focus object plane based on a position of the object when controlling the in-focus object plane.

10. The imaging apparatus as defined in claim 9, wherein the control section, in a distant observation mode, controls the image read mode so that a pixel binning read process is performed, and controls the in-focus object plane of the imaging section so that the in-focus object plane is set at a given position.

11. The imaging apparatus as defined in claim 10, wherein the control section, in a close observation mode, controls the image read mode so that an all-pixel read process is performed, and controls the in-focus object plane of the imaging section so that the in-focus object plane is determined based on a position of the object.

12. An endoscope system comprising:
   an imaging section that images an object;
   an observation mode setting section that sets an observation mode when the imaging section images the object; and
   a control section that switches an image read mode from a plurality of read modes in which an image is read from the imaging section and controls an in-focus object plane of the imaging section based on the observation mode set by the observation mode setting section; wherein
   the control section switches the image read mode from a distant observation mode and close observation mode, the distant observation mode performs a pixel binning read process, and the close observation mode performs an all-pixel read process;
   the control section, in a close observation mode, controls the in-focus object plane of the imaging section so that the in-focus object plane of the imaging section in the close observation mode is closer to the imaging section than that in the distant observation mode;
   the control section variably sets a depth of field by performing the pixel binning read process even if the in-focus object plane of the imaging section is fixed;
   a depth of field D1 is specified by a permissible circle of confusion corresponding to a pixel pitch of an imaging element included in the imaging section;
   a depth of field D2 is a depth of field in the distant observation mode; and
   the depth of field D1 and the depth of field D2 satisfying the relationship D2>D1.

13. The endoscope system as defined in claim 12, wherein the depth of field D2 in the distant observation mode is specified by a permissible circle of confusion corresponding to a pixel pitch when handling a plurality of pixels as one pixel.

14. A method of controlling an imaging apparatus, the method comprising:
   setting an observation mode when an object is imaged;
   switching an image read mode from a plurality of read modes in which an image is read from an imaging section based on the set observation mode;
   controlling an in-focus object plane of the imaging section based on the set observation mode; and
   controlling the imaging apparatus so that the imaging apparatus images the object based on the image read mode and the control of the in-focus object plane; wherein
   the switching switches the image read mode from a distant observation mode and close observation mode, the distant observation mode performs a pixel binning read process, and the close observation mode performs an all-pixel read process;
   in a close observation mode, the controlling controls the in-focus object plane of the imaging section so that the in-focus object plane of the imaging section in the close observation mode is closer to the imaging section than that in the distant observation mode;
   a depth of field is set by performing the pixel binning read process even if the in-focus object plane of the imaging section is fixed;
   a depth of field D1 is specified by a permissible circle of confusion corresponding to a pixel pitch of an imaging element included in the imaging section;
   a depth of field D2 is a depth of field in the distant observation mode; and
   the depth of field D1 and the depth of field D2 satisfying the relationship D2>D1.

* * * * *